United States Patent [19]

Sinn

[11] Patent Number: 5,386,908
[45] Date of Patent: Feb. 7, 1995

[54] PACKAGE FOR ENDOSCOPIC SUTURE SYSTEM

[75] Inventor: Hans-Jurgen F. Sinn, Fairfield, Conn.

[73] Assignee: United States Surgical Corporation, Norwalk, Conn.

[21] Appl. No.: 37,984

[22] Filed: Mar. 25, 1993

[51] Int. Cl.⁶ .............................................. B65D 85/20
[52] U.S. Cl. .................. 206/363; 206/63.3; 206/471
[58] Field of Search ............. 206/63.3, 363–365, 206/461, 470, 471

[56] References Cited

U.S. PATENT DOCUMENTS

| | | | |
|---|---|---|---|
| 3,910,410 | 10/1975 | Shaw | 206/471 |
| 3,983,996 | 10/1976 | Hendren, III | 206/363 |
| 4,106,621 | 8/1978 | Sorenson | 206/470 |
| 4,524,868 | 6/1985 | Buckley | 206/364 |
| 4,779,727 | 10/1988 | Taterka et al. | 206/364 |
| 5,082,112 | 1/1992 | Dunklee | 206/363 |
| 5,165,540 | 11/1992 | Forney | 206/364 |
| 5,226,535 | 7/1993 | Rosdhy et al. | 206/364 |

*Primary Examiner*—Jimmy G. Foster

[57] ABSTRACT

A package for an endoscopic suture system, the system including an elongated body, a suture, a needle attached to the suture, and a suture retainer, the suture further being connected to and extending from the elongated body, extending into a suture retainer and terminating in the needle. The package includes a first channel for receiving the elongated body and which is formed in a first plane. A second channel for receiving the suture retainer is formed in a plane below the first plane. A first plurality of flanges retain the elongated body in the first channel and a second plurality of flanges retain the suture retainer in the second channel.

10 Claims, 3 Drawing Sheets

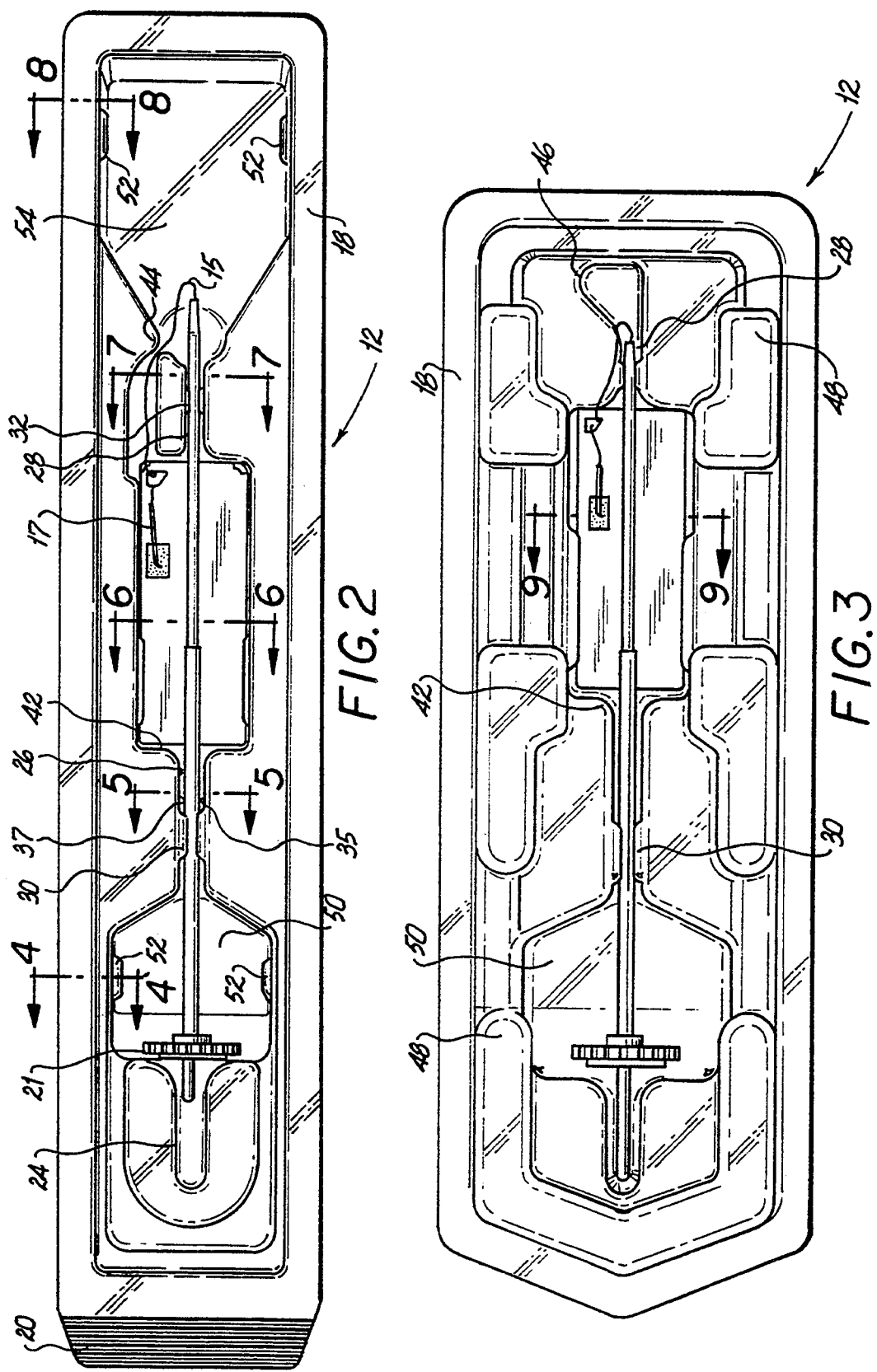

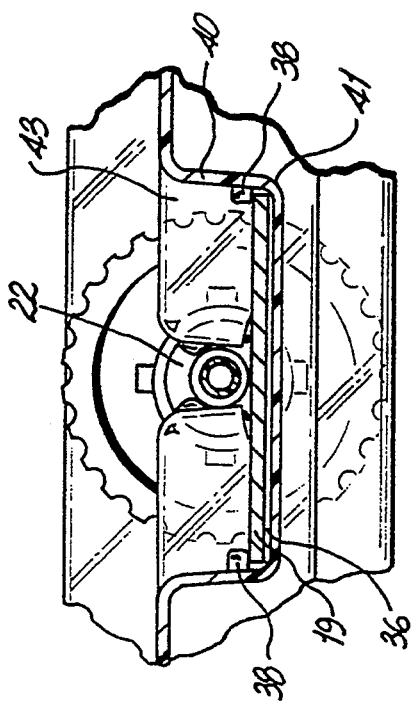
FIG. 6
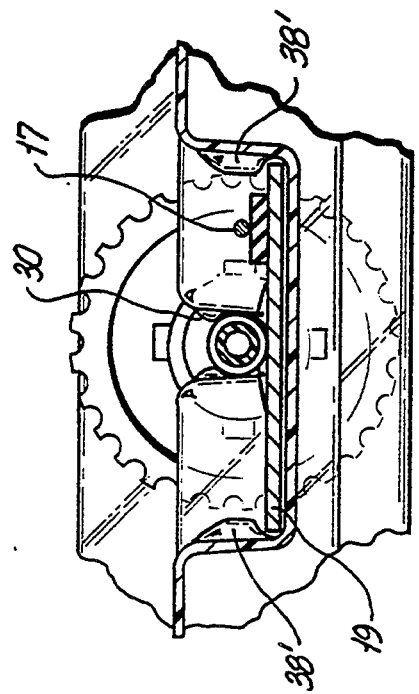
FIG. 9
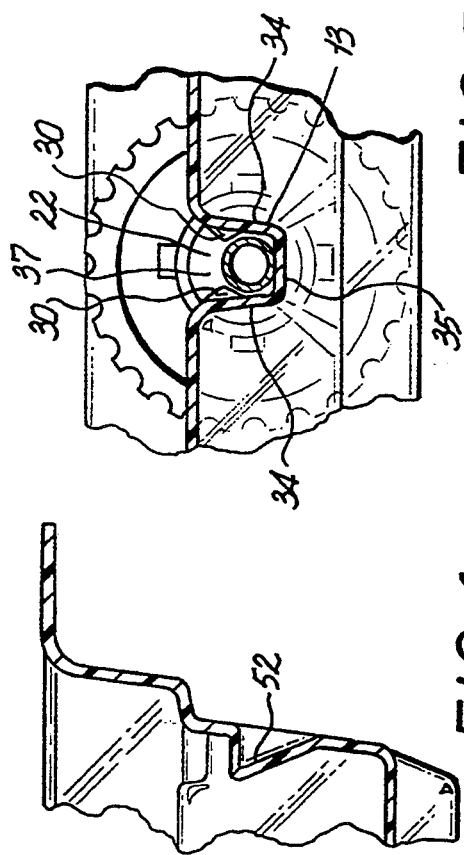
FIG. 5
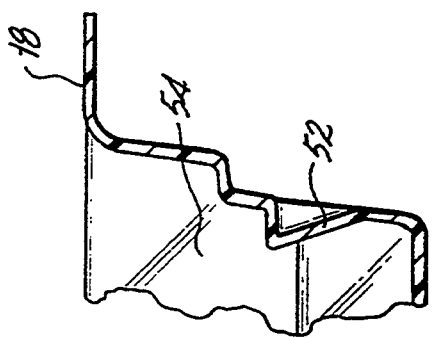
FIG. 8
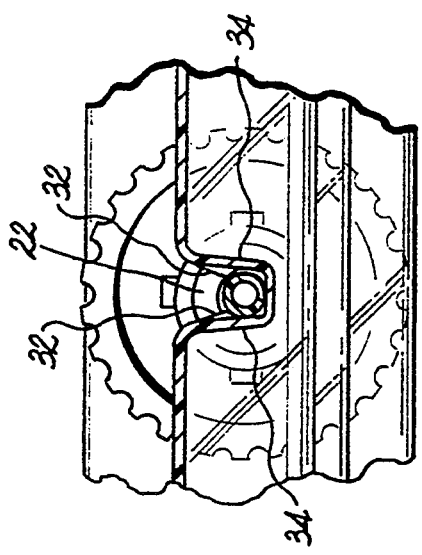
FIG. 7
FIG. 4

PACKAGE FOR ENDOSCOPIC SUTURE SYSTEM

BACKGROUND OF THE INVENTION

1. Field of the Invention

The present invention relates to a package for securely packaging and retaining an endoscopic suture system including both an endoscopic instrument and a suture retainer.

2. Background of the Art

Various types of instrument packages are known for separately packaging endoscopic surgical instruments and suture retainers. One example of a package for an elongated surgical instrument is shown in U.S. Pat. No. 4,324,331 which discloses a bottom assembly containing at least one cavity for receiving a surgical implement and a lid portion to cover the cavity. This package also includes a plurality of spaced apart cavities for selectively placing protective plugs at each end of the implement such that one packaging cavity may be used for various length instruments. Another example of a package for an elongated medical instrument is shown in U.S. Pat. No. 3,910,410 which discloses a tray having at least one cavity for receiving articles and a flange area upon which rests a lid for closing the at least one cavity. This package also includes two coatings of material for sealing the lid to the tray. Yet another example of a package for an endoscopic or elongated instrument is shown in U.S. Pat. No. 5,082,112 which discloses a packaging unit for an endoscopic ligating loop instrument, the packaging unit including a molded instrument holding member and a cover member.

With respect to packages for a suture, one example of such a suture retainer is shown in U.S. Pat. No. 5,123,528 which discloses a molded protective cover having an undulating cross-section which defines elongated tracks for receiving a suture portion. A backing panel is adhesively attached to the protective cover. Another example of suture package is shown in U.S. Pat. No. 5,099,994 which discloses a molded two piece suture package having an oval channel in which the sutures are wound.

The construction of a package for both an elongated surgical instrument and a suture retainer requires that the endoscopic instrument and suture retainer be securely held to prevent damage to the contents and the sterilized package. The package should also be constructed to permit relatively easy placement into the package and yet also be relatively easily releasable from the package by the user. It is also desirable that the package be economical to manufacture.

The present invention provides a package for an elongated surgical instrument and a suture retainer which provides the above properties.

SUMMARY OF THE INVENTION

Provided herein is a package for releasably holding a suture system comprising an elongated surgical instrument having an elongated body, suture connected to and extending from the elongated body, and a needle attached to the suture. The package includes a relatively rigid instrument holding member having a base. A cover member is mounted to a first plane of the instrument holding member and encloses the holding member. A first channel for receiving the elongated body is formed in a second plane, below the first plane, of the instrument holding member and conforms to the general shape of the elongated body. The elongated body is retained in the first channel by at least one pair of body flanges which extend from the side walls of the first channel. The body flanges are rigid enough to retain the elongated body and yet flexible enough to deflect when the instrument is inserted into and removed from the first channel.

The package also includes a second channel formed in a third plane, below the second plane, of the instrument holding member. The second channel conforms to the general shape of the suture retainer and receives the suture retainer therein. At least one pair of oppositely positioned retainer flanges extend from the side walls of the second channel to frictionally engage or retain the suture retainer in the second channel.

The package also includes at least one release channel for facilitating the gripping of the elongated body. An additional release channel may also be formed by the second channel to provide an additional channel for one to grip the elongated body of the instrument. A further feature of the invention is a suture channel for receiving the portion of the suture extending from the elongated body into the retainer.

BRIEF DESCRIPTION OF THE DRAWINGS

The accompanying drawings constitute part of the disclosure of the invention and illustrate preferred embodiments of the invention. The drawings may be briefly described as follows:

FIG. 2 is a plan view of the package shown in FIG. 1;

FIG. 3 is a plan view of an alternative package in accordance with the present invention;

FIG. 4 is a cross-sectional view of the instrument holding member of the package taken along the line 4—4 of FIG. 2;

FIG. 5 is a cross-sectional view of the instrument holding member of the package taken along line 5—5 of FIG. 2;

FIG. 6 is a cross-sectional view of the instrument holding member of the package taken along line 6—6 of FIG. 2;

FIG. 7 is a cross-sectional view of the instrument holding member of the package taken along line 7—7 of FIG. 2;

FIG. 8 is a cross-sectional view of the instrument holding member of the package taken along line 8—8 of FIG. 2; and FIG. 9 is a cross-sectional view of the instrument holding member of the package taken along line 9—9 of FIG. 3.

DETAILED DESCRIPTION OF PREFERRED EMBODIMENT

Figure 1:
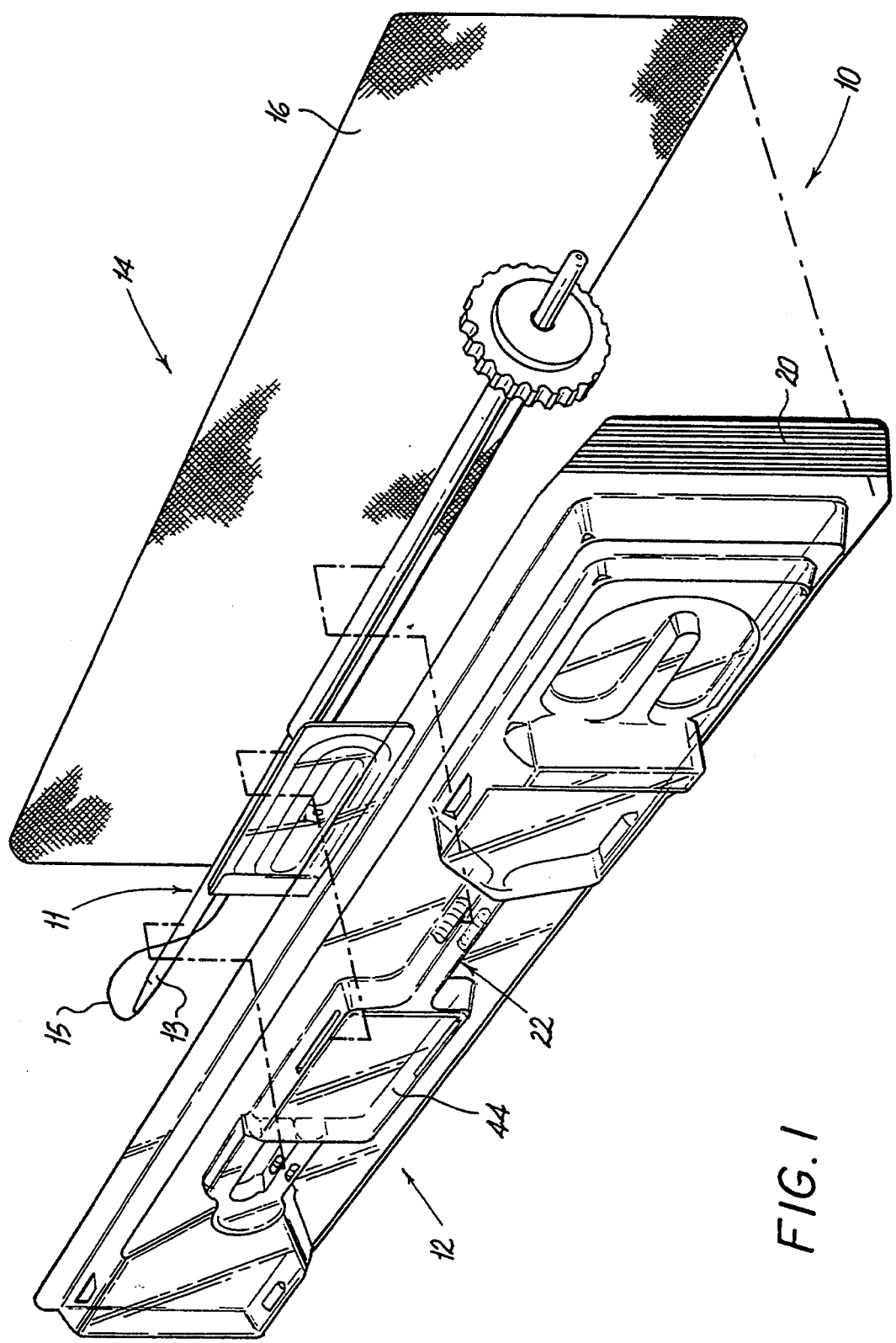
FIG. 1 is an exploded perspective view of the package of the present invention shown in combination with a suture system having an enlongated portion.

The package of the present invention provides means for packaging an elongated surgical instrument and a suture retainer in a manner which prevents damage during transportation and storage, yet permits convenient removal by the user when desired. The surgical instruments for which this package is specifically designed are elongated and relatively narrow so that they may be inserted through a trocar cannula for use in minimally invasive surgical procedures, such as laparoscopic or endoscopic procedures.

Referring to the first embodiment of the invention shown in FIGS. 1 and 2, an endoscopic suture system package 10 for holding an endoscopic suture system 11 is shown. The endoscopic suture system includes an elongated tubular body 13, a suture 15 and a needle 17 attached to the suture 15. The suture 15 is retained in a suture retainer 19. The suture 15 extends from and is connected to one end of elongated body 13 and terminates at needle 17. One type of such an endoscopic suture system is a SURGIWIP disposable suture ligature with delivery system sold by United States Surgical Corporation. Alternatively, the suture may be unattached to a needle which could be packaged separately in or out of the package in the present invention.

The package 10 includes a relatively rigid molded instrument holding member 12 and a peelable or strippable cover member 14 which is capable of maintaining the sterile condition of the package contents. Instrument holding member 12 and cover member 14 can be fabricated from any suitable materials. Advantageously, instrument holding member 12 is molded from a resin and preferably a transparent recycleable resin, such as polyethylene terephthalate. Cover member 14 is advantageously formed from a spunbonded material, e.g., of high density polyethylene fiber, such as Tyvek ® (DuPont) which is ideal for ethylene oxide sterilization. Numerous other materials, both polymeric, non-polymeric and combinations thereof, e.g., aluminum foilpolymer laminates, can be utilized for the construction of instrument holding member 12 and/or cover member 14 as will be readily appreciated by those skilled in the art. In the sealed condition of the package, cover member 14 is bonded along its perimeter region 16 to perimeter region 18 of instrument holding member 12 employing any suitable adhesive. The perimeter region 18 of the instrument holding member 12 is formed in a first and uppermost plane of the rigid instrument holding member 12. A knurled section 20 at the proximal end of instrument holding member 12 facilitates gripping of this member with one hand and pulling back of cover member 14 with the other.

The rigid instrument holding member 12 includes a first channel 22 which extends for at least the full length of the elongated tubular body 13 and prevents the body 13 from shifting about in the package, preferably through frictional engagement with the elongated tubular body 13. As will be appreciated, the first channel 22 need not be continuous over the length of the package. In the preferred embodiment the first channel 22 includes a proximal portion 24, a middle portion 26 and a distal portion 28. The first channel 22 includes a pair of oppositely positioned side walls 34, a bottom wall 35 and an open top 37. The first channel 22 is formed in a second plane which is below the first plane of the holding member perimeter 18. The elongated tubular body 13 is retained within the first channel 22 by a first and second pair of flanges 30 and 32, respectively, which extend over a portion of the first channel 22. As best seen in FIG. 5, the first pair of flanges 30 extend oppositely from the side walls 34 of the middle portion 26 of first channel 22 to hold the middle portion of the elongated instrument. The flanges are preferably integral with the side walls 34, and are rigid enough to retain the tubular body 13 in the first channel 22, but sufficiently flexible to deflect when the elongated tubular body 13 is inserted into or removed from the first channel by being frictionally forced through the flanges 30. As shown in FIG. 2 and FIG. 7, the second pair of flanges 32 extend from the sides walls 34 of the distal portion 28 of first channel 22 to retain the distal end of the elongated tubular body 13 within the first channel 22.

Referring to FIGS. 2 and 3, a suture retainer channel 36 is formed in a third plane below the second plane in which first channel 22 is formed. The suture retainer channel 36 conforms to the general shape of the suture retainer 19 which is retained therein. The suture retainer channel is formed by side walls 40, a bottom wall 41, and an open top 43. The suture retainer 19 is frictionally retained in the retainer channel 36 by a pair of oppositely positioned retainer flanges 38. As best seen in FIGS. 6 and 9, the retainer flanges 38 extend from the side walls 40 of suture retainer channel 36 and are integral therewith. The retainer flanges 38 are rigid enough to retain the suture retainer 19 within the suture retainer channel 36, but flexible enough to deflect somewhat when the retainer 19 is inserted into or, if desired, removed from the retainer channel 36. The suture retainer channel 36 also acts as a well to facilitate the gripping and removal of the elongated tubular body 13 from the instrument holding member 12. Further, the suture retainer channel 36 is in communication with the first channel 22 between the middle portion 26 and distal portion 28 of the first channel 22.

Referring to FIG. 2, a suture channel 44 is formed in approximately the same plane as the first channel 22 and generally conforms to the arched shape of the suture extending from the elongated tubular body 13 and doubled back into the suture retainer 19. The suture channel 44 communicates with the first channel 22 and the suture retainer channel 36 so as to maintain the suture 15 in substantially the same plane throughout the endoscopic suture instrument 11.

The package 10 also includes at least one release channel 50 formed in the second, or first channel, plane. The release channel 50 could also be formed in a plane below the third, or suture retainer, plane. The release channel 50 receives the knob or handle 21 of the endoscopic suture system 11. In the embodiment shown in FIGS. 2 and 4 the release channel 50 includes a pair of nesting lugs 52 which permit the instrument holding member 12 to be stacked, and yet easily disengaged from one another when they are empty. As shown in FIGS. 2 and 8, a corresponding pair of nesting lugs 52 are provided in a well 54 to balance empty instrument holding members when they are stacked.

Referring to the embodiment shown in FIG. 3, the instrument holding member 12 has many similar features to the one shown in FIG. 2, with one difference being an alternative suture channel 46' which provides an area for the receipt of the suture 15. Also the suture retainer flanges 38' are more elongated and extend further up the side walls 40 towards the open top 43 for greater frictional engagement. Another feature of the embodiment shown in FIG. 3 is that standoffs 48 are formed in the instrument holding member 12 in a plane above the first plane which is the one in which the holding member perimeter 18 is extends. The standoffs 48 facilitate circulation of sterilization gases during sterilization of the package 10 and its contents.

In use, the endoscopic suture system is loaded into the rigid instrument holding member by first inserting the suture retainer 19 containing suture 15 into the retainer channel 36 and engaging the suture retainer 19 under the retainer flanges 38. The suture 15 extending between the suture retainer 19 and the elongated body 13 is then placed in the suture retainer channel 36. The distal-most portion of elongated body 13 is then placed in the distal portion 28 of the first channel 22 and frictionally engaged by the second pair of flanges 32. The middle portion of the elongated body 13 is then placed in the middle portion 26 of the first channel 22 and frictionally engaged by the first pair of flanges 30. The knob 21 of the suture system is inserted into the release channel 50 and a cover 14 is then applied to the instrument holding member 12.

The endoscopic suture system is released from the instrument holding member 12 by first grasping the portion of the elongated body 13 positioned above the release channel 50. The above steps are then reversed and the elongated body 13 is removed from its engagement by the first pair of flanges 30 and then from its engagement by the second pair of flanges 32. The suture retainer 19 is released from its engagement by the retainer flanges 38 by grasping preferably a distal end 42 of the suture retainer 19 and removing it from its engagement by the retainer flanges 38. Removing the distal end 42 of the suture retainer 19 presents possible withdrawal of the suture 15 from the suture retainer 19 or the elongated body 13. A lternatively, the surgeon could grip the needle 17 and remove it from the suture retainer 19 without removing the retainer 19 from the package 10.

Having now described the invention in specific detail and exemplified the manner in which it may be carried into practice, it will be readily apparent to those skilled in the art that innumerable variations, applications, modifications, and extensions of the basic principles involved may be made without departing from its spirit or scope. By way of example only, the depth width and relative position of the channels may vary width based on personal preference and the particular suture system to be packaged. Thus, it is contemplated that the suture enters the retainer immediately adjacent the distal end of the elongated body, thereby reducing the distance over which the suture is exposed extending from the elongated body to the suture retainer.

What is claimed is:

1. A package for an endoscopic suture system, said system including an elongated body, a suture, a suture retainer and a needle attached to said suture and said retainer, the package comprising:
   a substantially rigid instrument holding member having a base; an elongated body channel in the base of the instrument holding member for receiving said elongated body,
   a retainer channel in the base of the instrument holding member for receiving said retainer, said body and retainer channels each defined by a pair of oppositely positioned side walls, a bottom wall and an open top, said body channel being formed in a first plane and said retainer channel being formed in a second plane below said first plane;
   a pair of oppositely positioned body flanges for frictionally engaging said body in said body channel, said body flanges each extending from said body channel side walls across a portion of said body channel open top;
   a pair of oppositely positioned retainer flanges for frictionally engaging said retainer in said retainer channel, said retainer flanges extending from said retainer channel side walls into a portion of said retainer channel, said body flanges configured to be rigid enough to retain said tubular body, yet flexible enough to deflect when said elongated body or retainer is pulled through said elongated body flanges;
   a release channel for facilitating the gripping of a first portion of said elongated body and said retainer, and further facilitating its removal from the package;
   a second release channel for facilitating the gripping of a second portion of said elongated body; and
   a cover member adapted to be mounted to and to enclose the instrument holding member.

2. The package as in claim 1 further comprising a receiving channel for receiving a portion of said suture extending from said elongated body.

3. The package as in claim 1 further comprising a plurality of flanges for retaining a distal end of the elongated body in said elongated body channel.

4. The package as in claim 1 wherein said elongated body channel and said retainer channel are dimensioned to correspond to the general shape of the ligating system.

5. A package as in claim 1 wherein said body flanges are integral with said elongated body channel and said retainer flanges are integral with said retainer channel.

6. A package as in claim 1 wherein said package is formed of a substantially rigid material.

7. A package as in claim 1 further comprising a suture channel for receiving a portion of the suture which extends from said elongated body into said retainer.

8. The package of claim 1 wherein said cover member is adhesively bonded to an upper surface of said package such that said cover member can be peeled away from the upper surface of said package.

9. The package of claim 1 wherein said package is fabricated from a transparent plastic.

10. The package of claim 1 wherein said package is fabricated from polyethylene terephthalate.

* * * * *